Figure 1:
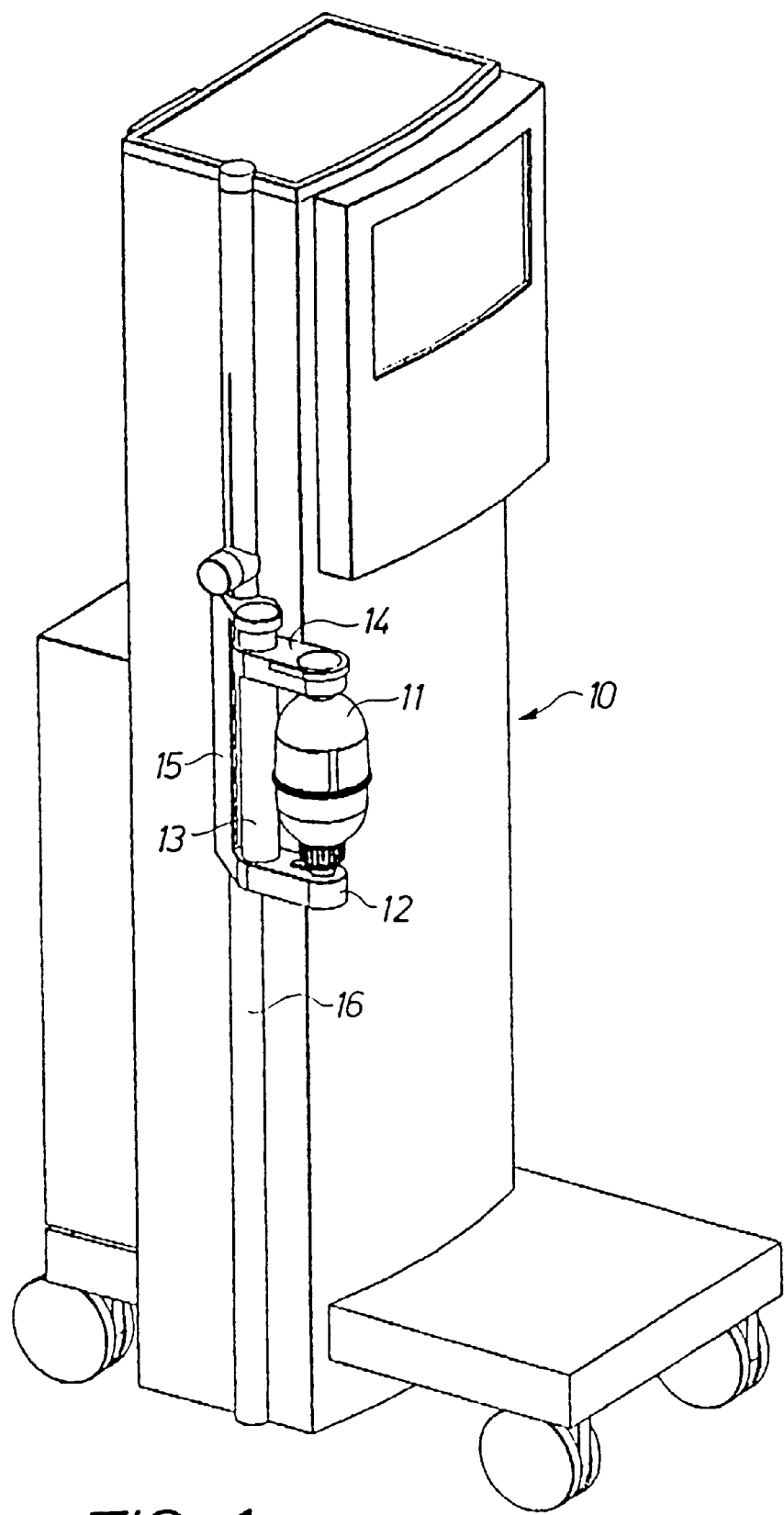

United States Patent [19]
Carlsson et al.

[11] Patent Number: 6,036,858
[45] Date of Patent: Mar. 14, 2000

[54] DEVICE IN A DIALYSIS MACHINE

[75] Inventors: Per-Olov Carlsson; Bjorn Gillerfalk, both of Ronneby; Thore Falkvall, Helsingborg, all of Sweden

[73] Assignee: Althin Medical AB, Ronneby, Sweden

[21] Appl. No.: 08/983,592

[22] PCT Filed: Jul. 3, 1996

[86] PCT No.: PCT/SE96/00897

§ 371 Date: Apr. 27, 1998

§ 102(e) Date: Apr. 27, 1998

[87] PCT Pub. No.: WO97/02056

PCT Pub. Date: Jan. 23, 1997

[30] Foreign Application Priority Data

Jul. 3, 1995 [SE] Sweden ................................ 9502397

[51] Int. Cl.[7] .................................................. B01D 61/30
[52] U.S. Cl. .................... 210/232; 210/321.71; 210/541; 210/646; 248/311.2; 248/313; 604/4
[58] Field of Search ............... 210/232, 321.71, 210/541, 646, 647; 248/311.2, 312, 312.1, 313; 604/4–6

[56] References Cited

U.S. PATENT DOCUMENTS

| | | | |
|---|---|---|---|
| 3,872,868 | 3/1975 | Kline | 248/311.2 |
| 4,005,844 | 2/1977 | Richmond | 248/313 |
| 4,387,873 | 6/1983 | Pavlo et al. | 248/311.2 |
| 4,676,467 | 6/1987 | Palsulich | 248/311.2 |
| 5,275,724 | 1/1994 | Bucchianeri et al. | 210/321.71 |
| 5,641,144 | 6/1997 | Hendrickson et al. | 604/4 |
| 5,770,064 | 6/1998 | Jonsson et al. | 210/232 |

FOREIGN PATENT DOCUMENTS

| | | |
|---|---|---|
| 0278100 | 8/1988 | European Pat. Off. . |
| 0481257 | 4/1992 | European Pat. Off. . |
| 4138140 | 5/1993 | Germany . |

Primary Examiner—Joseph W. Drodge
Attorney, Agent, or Firm—James Ray & Associates

[57] ABSTRACT

A device in a dialysis machine for exchangeable connection of a powder cartridge (11) between an inlet (56') and an outlet (56) for liquid. The inlet and the outlet are provided in one and the other, respectively, of two jaws (12, 14), and at least one of these is guided for linear displacement towards and away from the other one for engaging the jaws with the powder cartridge (11) under connection of the inlet and the outlet to a hollow stud (18, 19; 31) on the powder cartridge positioned between the jaws for conducting liquid through the cartridge, or for interengaging of the jaws for short circuit of the inlet and the outlet.

15 Claims, 16 Drawing Sheets

DEVICE IN A DIALYSIS MACHINE

This application is a 371 PCT/SE96/00897, filed Jul. 3, 1995.

EP-B1 0 278 100 describes a dialysis system wherein the dialysis liquid is prepared at the site of use from a powder (sodium bicarbonate) which is supplied in a closed container—cartridge—which is inserted into a holder on the machine and is connected to an inlet for water and an outlet for the concentrated solution of the powder, which is obtained when water flows through the cartridge and dissolves the powder. This liquid concentrate then is added in an accurately measured amount to a water flow in the machine for obtaining dialysis liquid having the required concentration.

In a dialysis machine available on the market, which operates with this system, Gambro AK 100, the cartridge is inserted between two jaws pivotally mounted on a vertical wall of the machine one above the other, one of these jaws having an inlet for water and the other an outlet for the liquid concentrate obtained by dissolving the powder in the cartridge when water is allowed to flow through the cartridge. Then, the inlet and the outlet are connected to hollow studs which are provided at the ends of the cartridge. The connection takes place by penetrating membranes which are provided on the hollow studs and close these studs. The upper jaw is swung upwards when the cartridge is to be located between the jaws or is to be removed from this position after the powder in the cartridge having been consumed, but the jaws can also be swung towards said wall of the machine, the upper jaw downwards and the lower jaw upwards, in order that the inlet and the outlet, respectively, shall be connected with two connection pieces on the wall which are dimensioned in the same manner as the hollow studs on the cartridge. Between these connection pieces there is provided a short-circuit conduit so that liquid can flow from one jaw to the other via the short-circuit conduit without passing through a cartridge positioned between the jaws. This short-circuit connection is used also when the machine between two dialysis treatments following one upon the other has to be rinsed and disinfected by circulating a flow of disinfection liquid through the machine.

When a dialysis treatment has been effected there is always left some liquid in the cartridge. When the cartridge after a completed dialysis treatment is removed from the prior art dialysis machine it can therefore not be avoided that this liquid flows out onto the lower jaw and soils this jaw and above all the sealing ring or sealing rings which are provided in the jaw to seal around the hollow studs on the cartridge. When the water evaporates precipitated powder remains on the sealing rings. This will not be removed by the rinsing cycle because the sealing rings then are operative to seal around the short-circuit connection pieces on the machine. Precipitation or deposition of powder on the sealing rings causes increased wear of the sealing rings and reduces the sealing ability thereof so that they often have to be exchanged. In the prior art dialysis machine exchange of the rings is cumbersome and requires time consuming mounting work.

The purpose of the invention is to eliminate these drawbacks by providing a device of the kind mentioned above which makes possible that the sealing rings which shall seal between the hollow studs of the cartridge and the inlet and the outlet, respectively, are exposed during the rinsing and disinfection cycle to be rinsed and disinfected, and wherein the sealing rings are mounted on the jaws in such a manner that they can be exchanged in a simple manner when required without extensive demounting and mounting work being required.

The purposes mentioned above are achieved by the according to the invention having obtained the characterizing features of claim 1.

Figure 2:
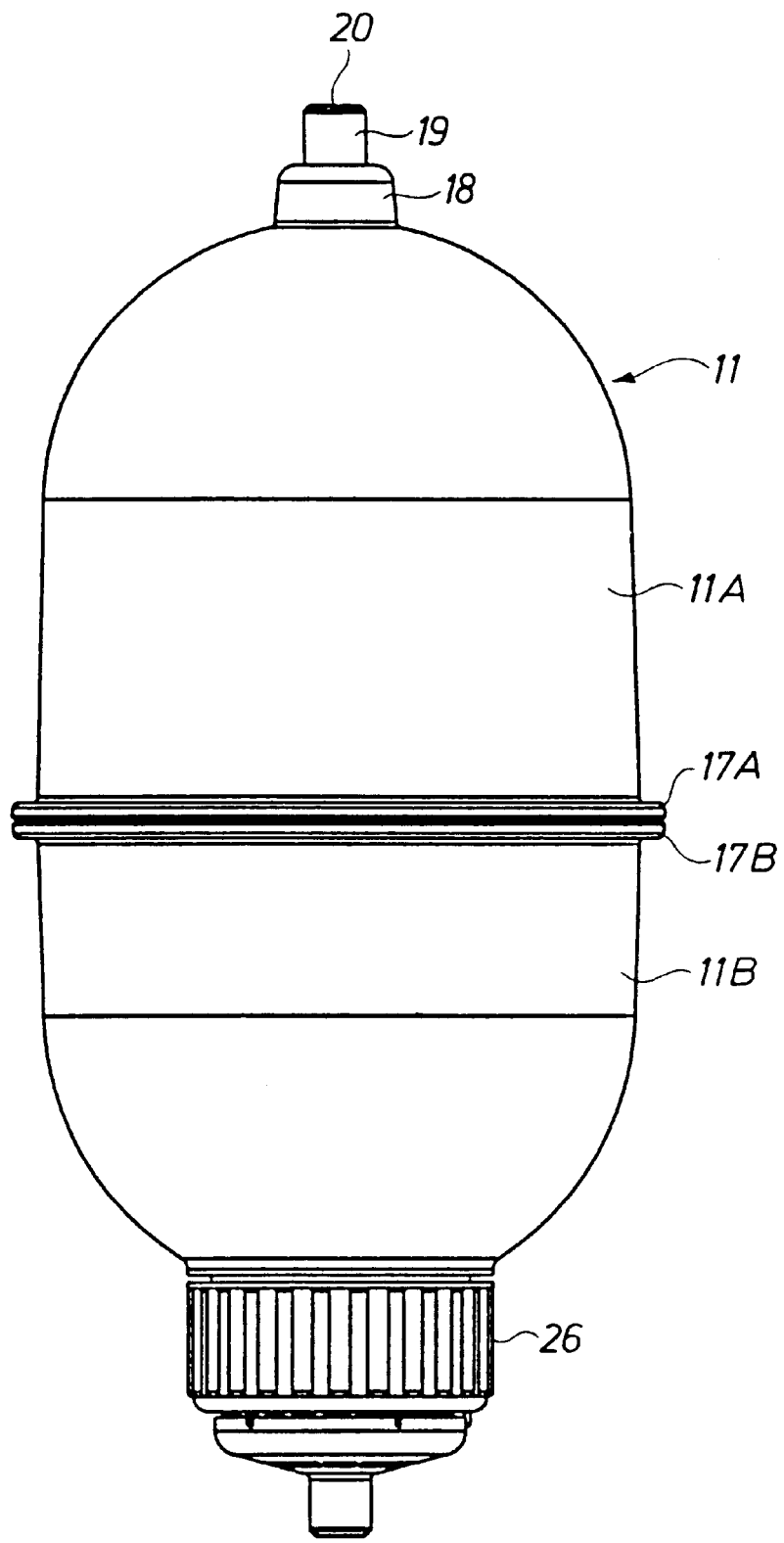
Figure 3:
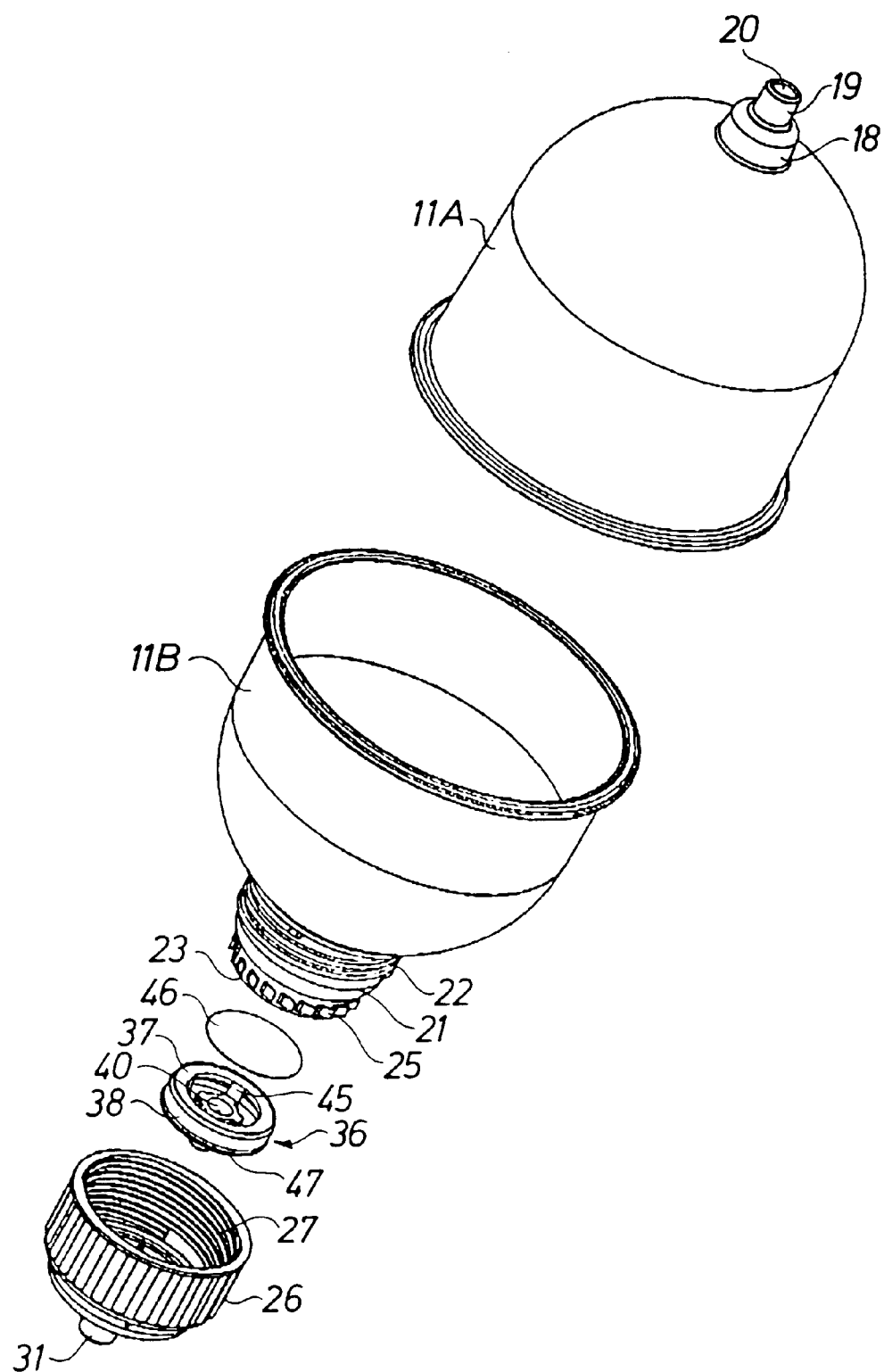
Figure 4:
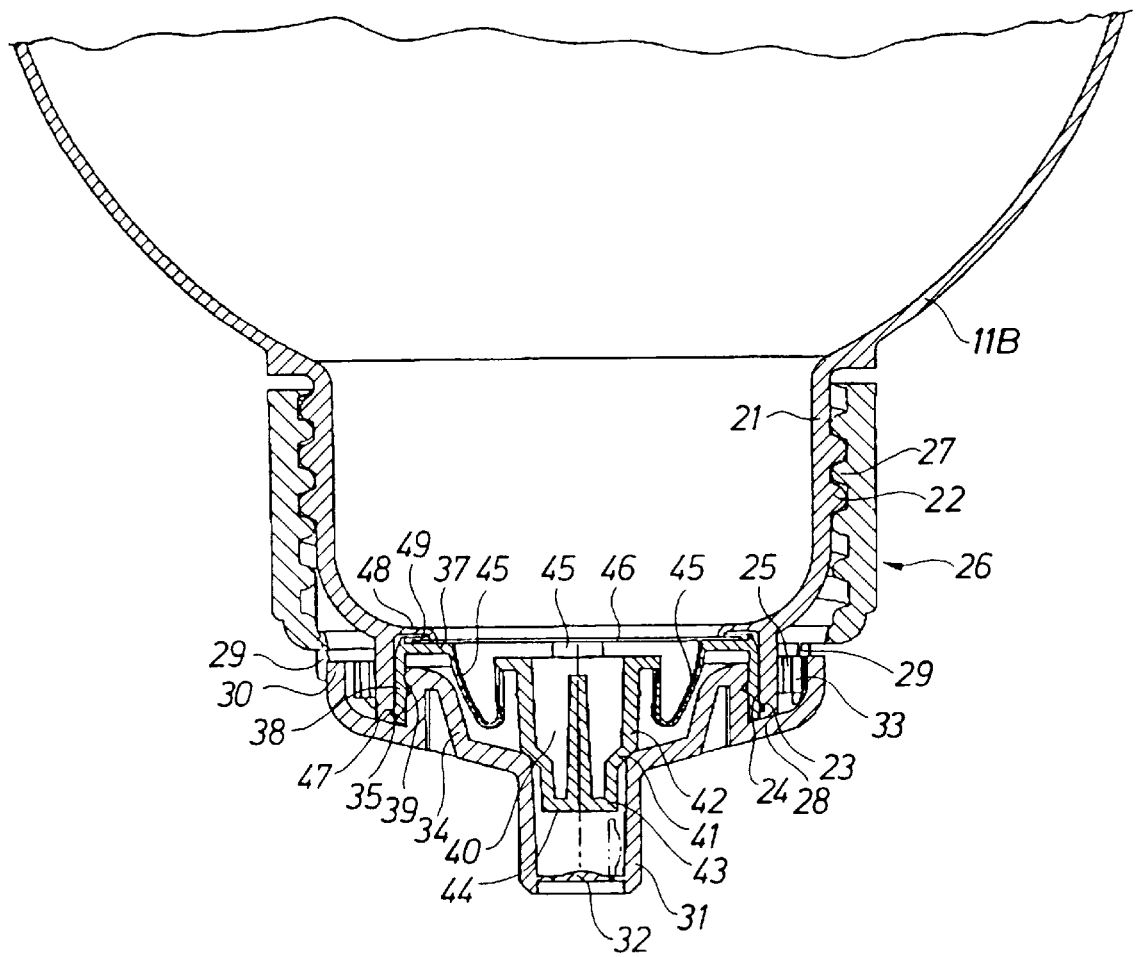
Figure 5:
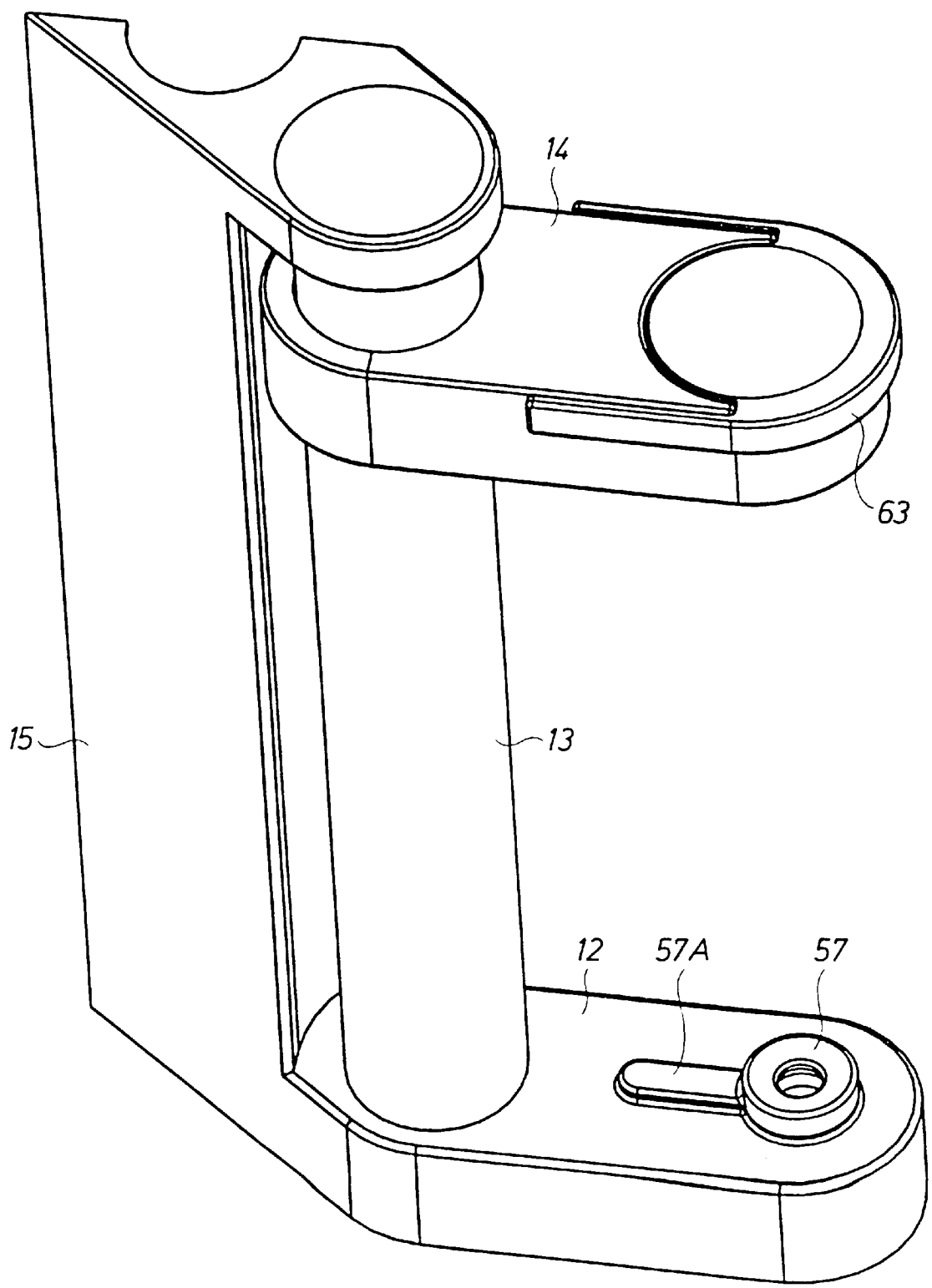
Figure 6:
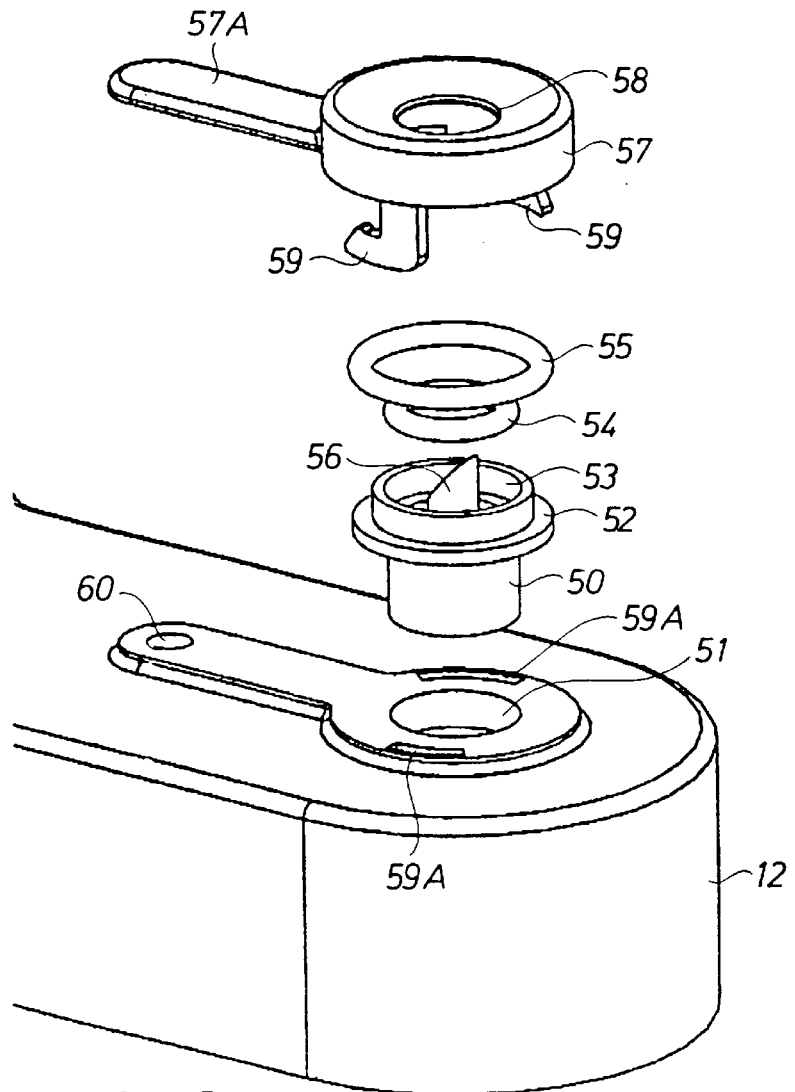
Figure 7:
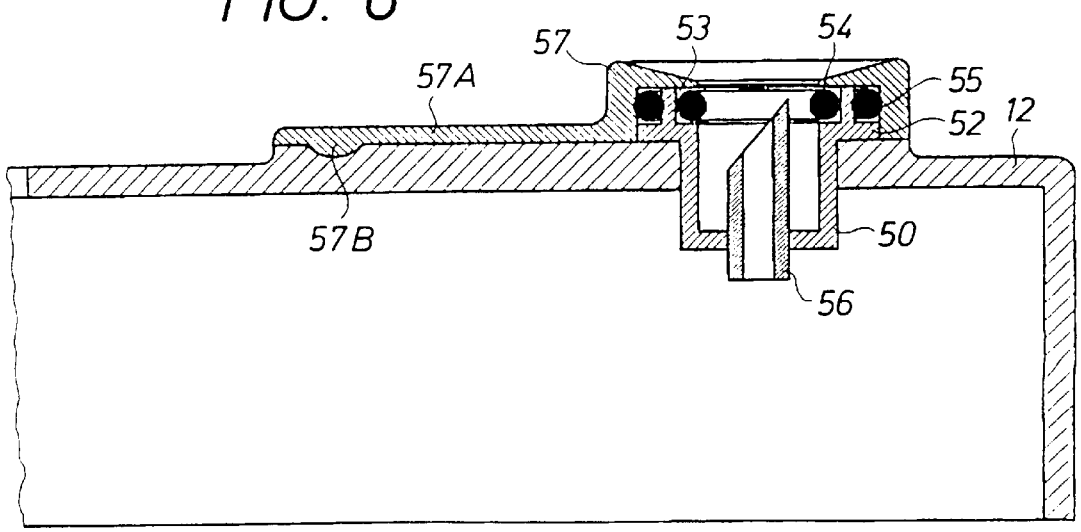
Figure 8:
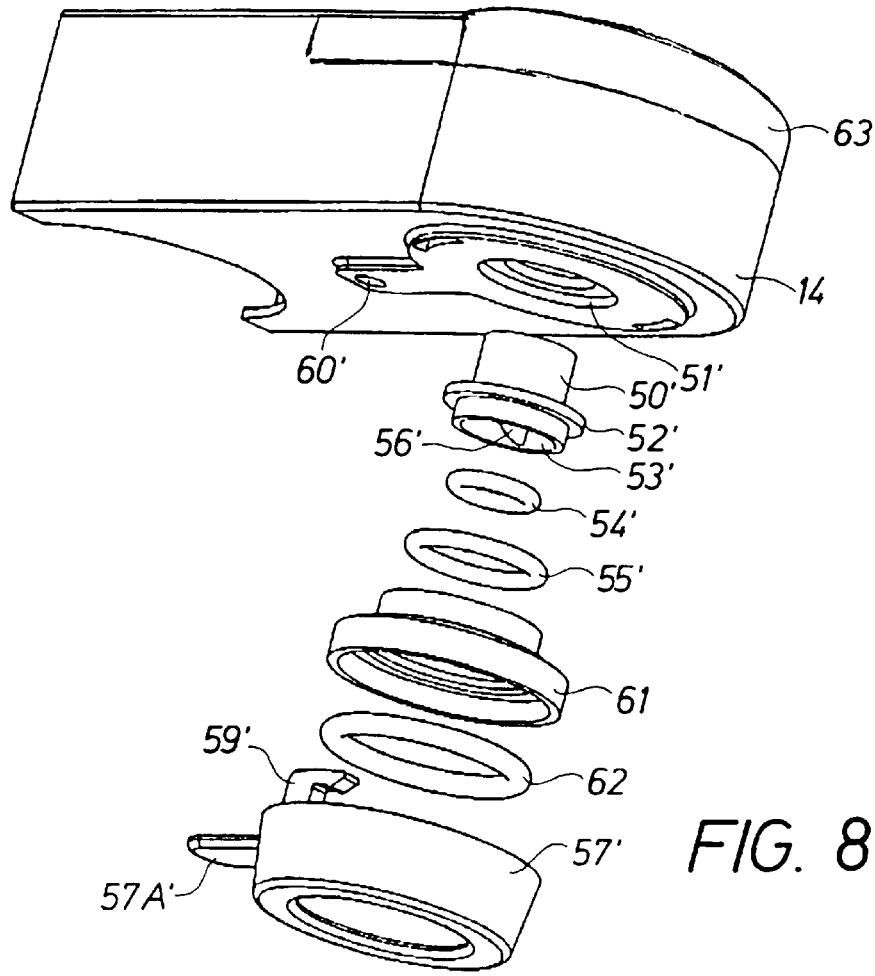
Figure 9:
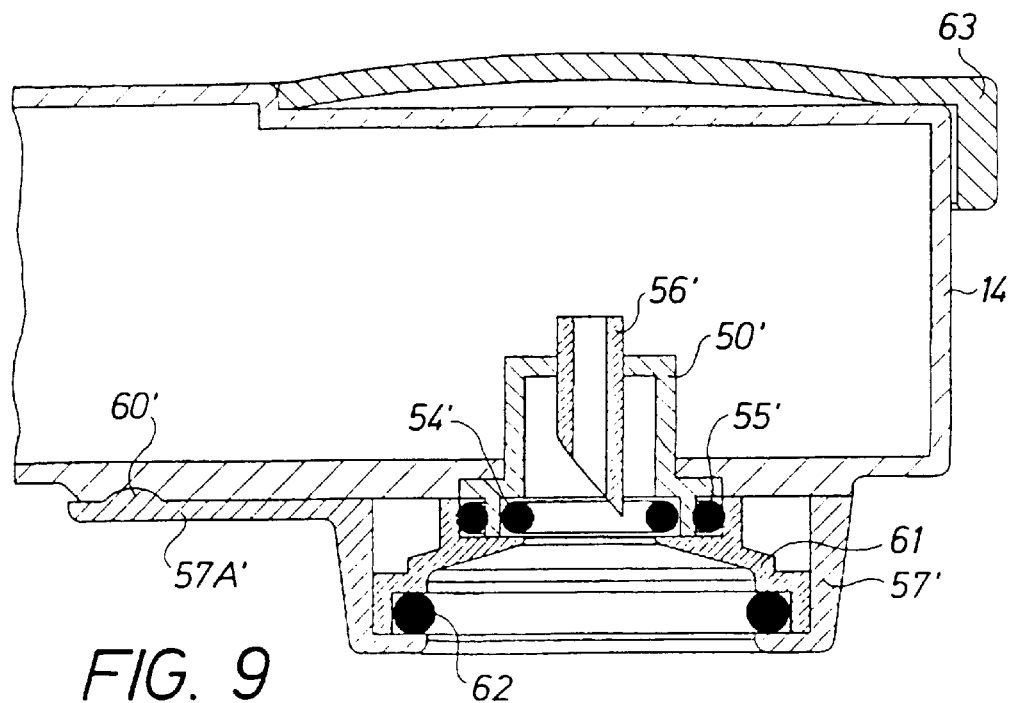
Figure 10:
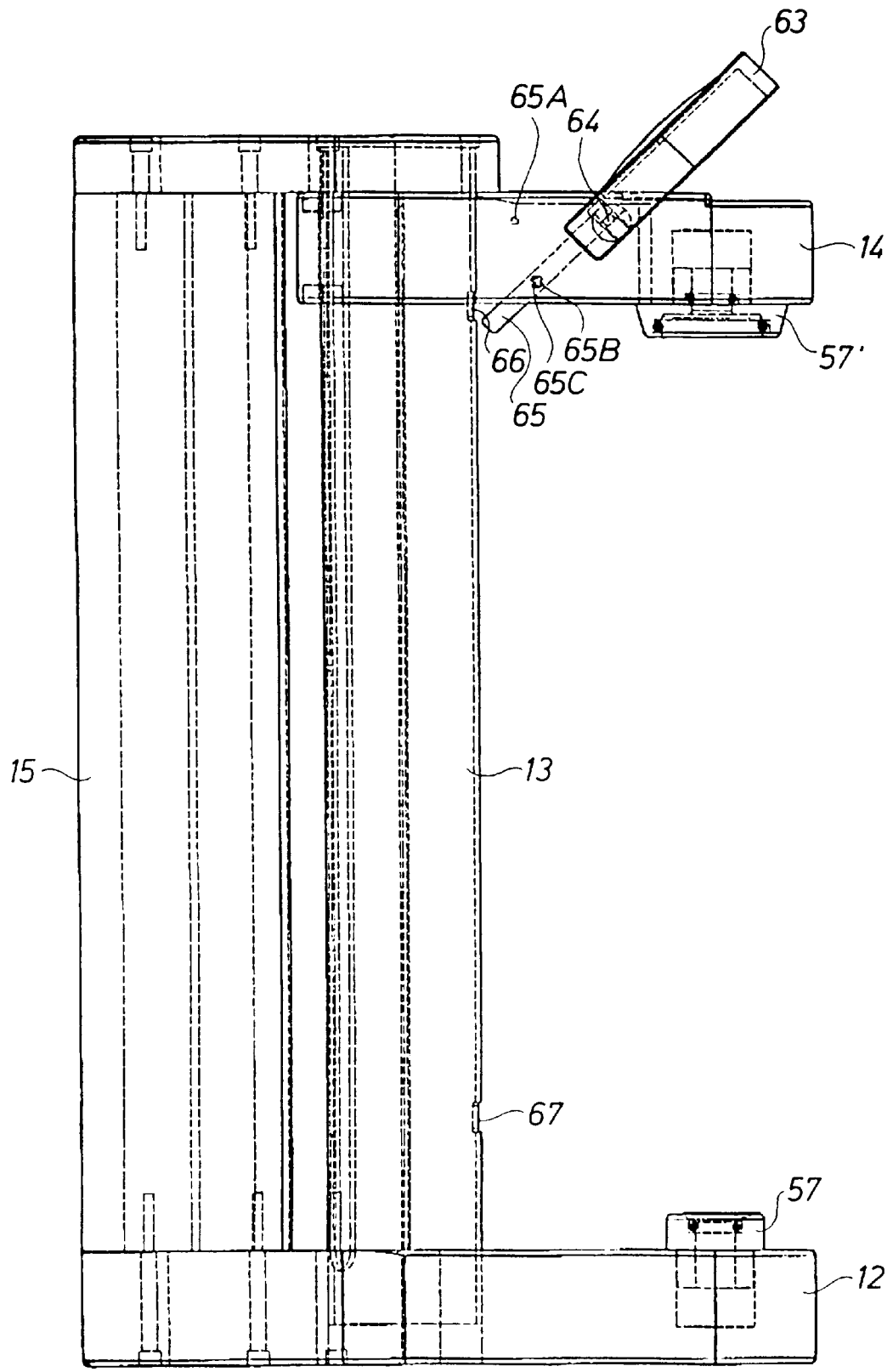
Figure 11:
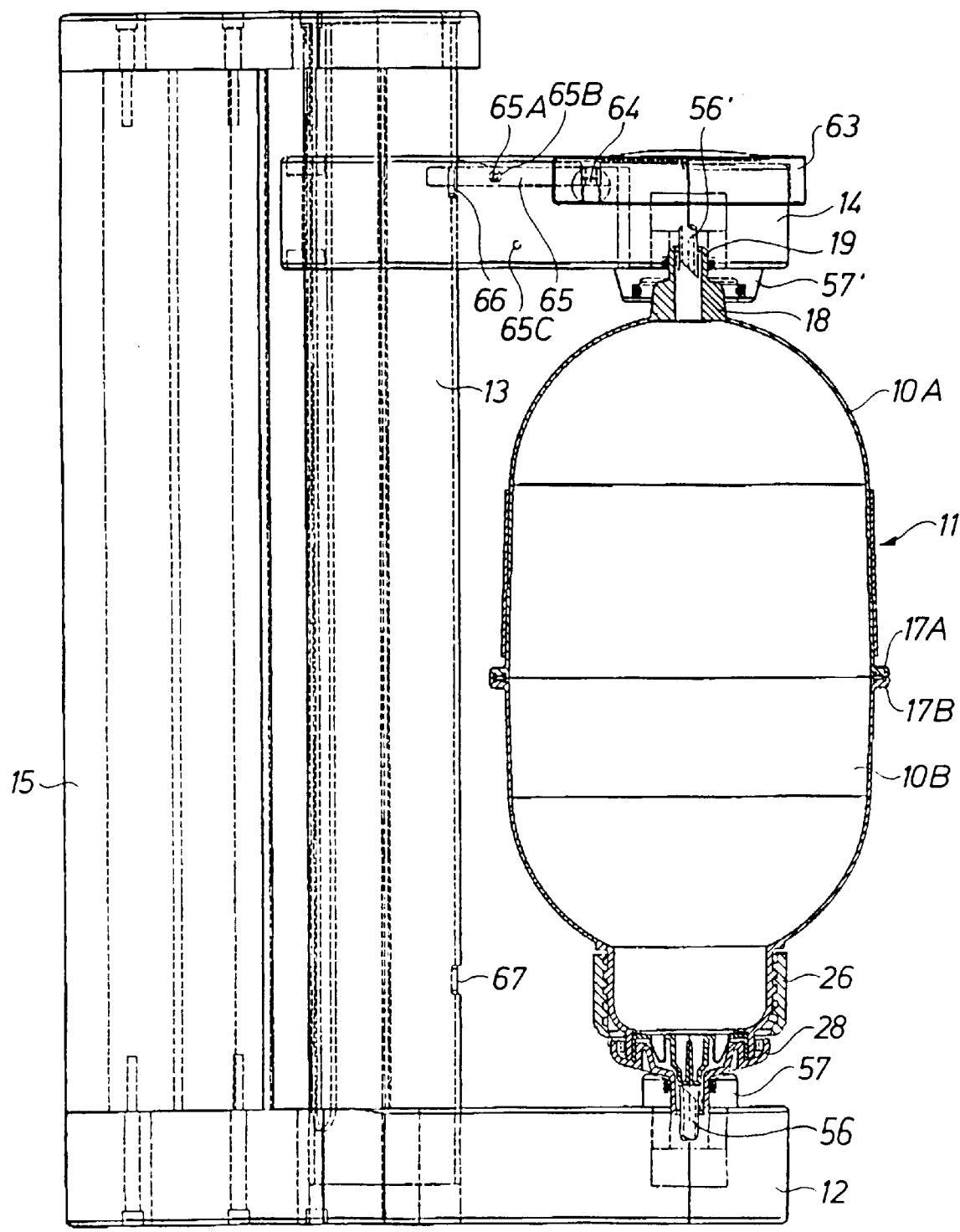
Figure 12:
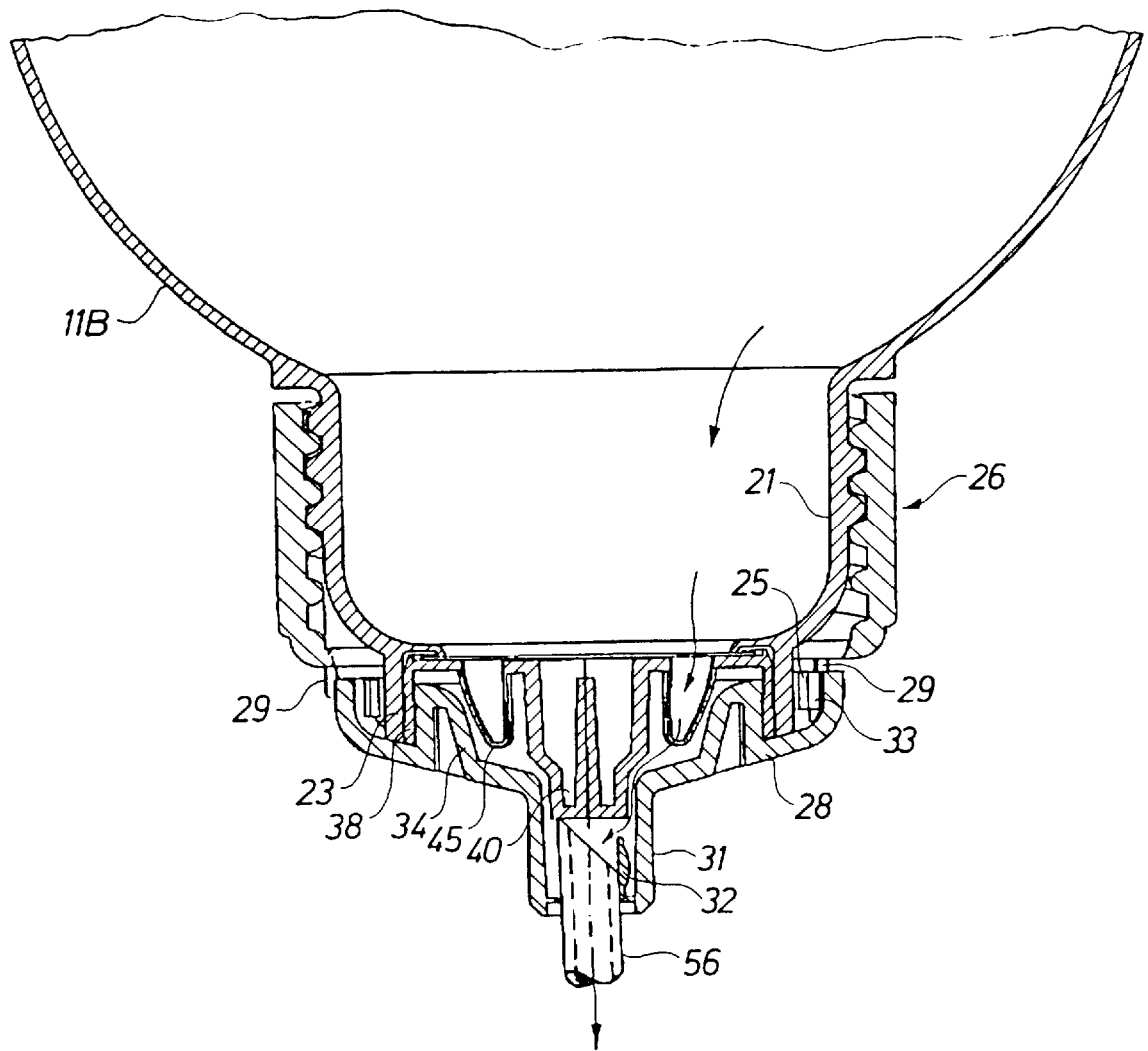
Figure 13:
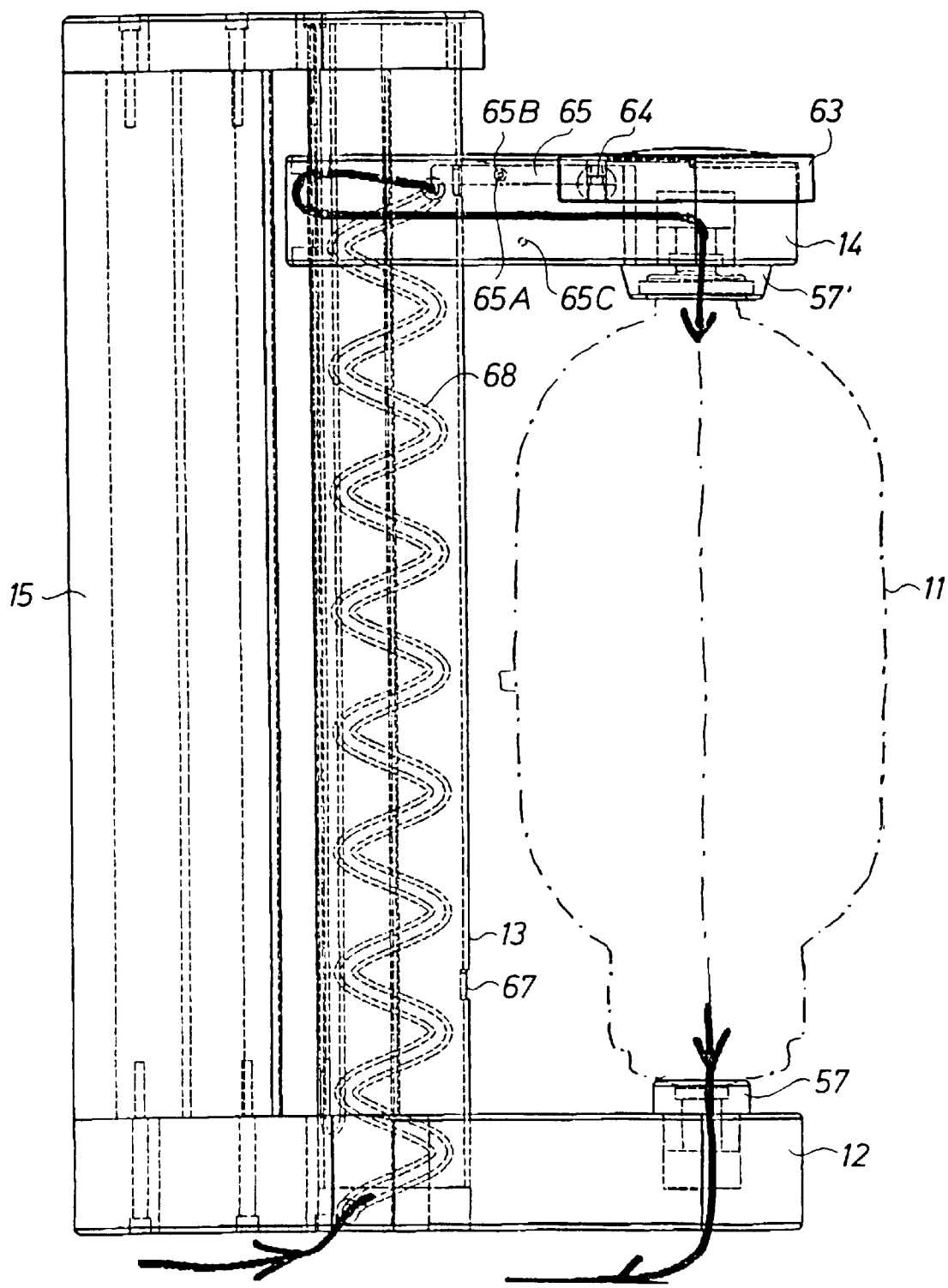
Figure 14:
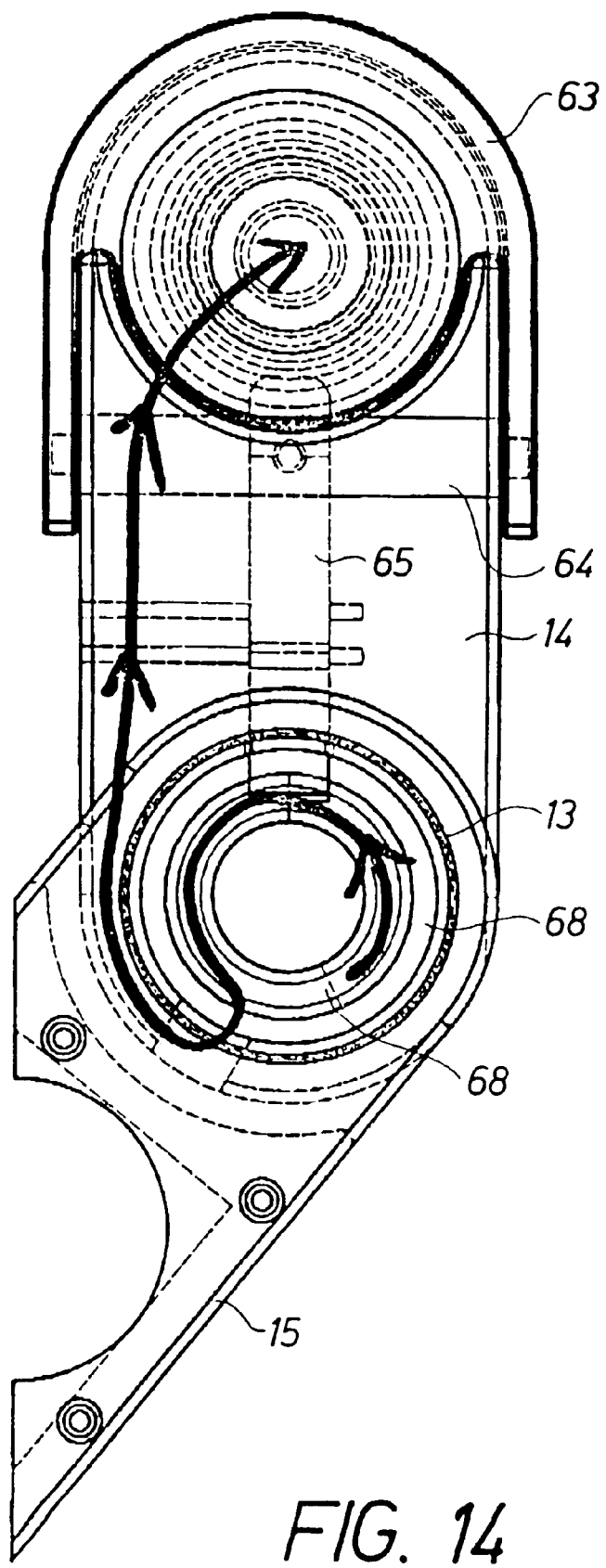
Figure 15:
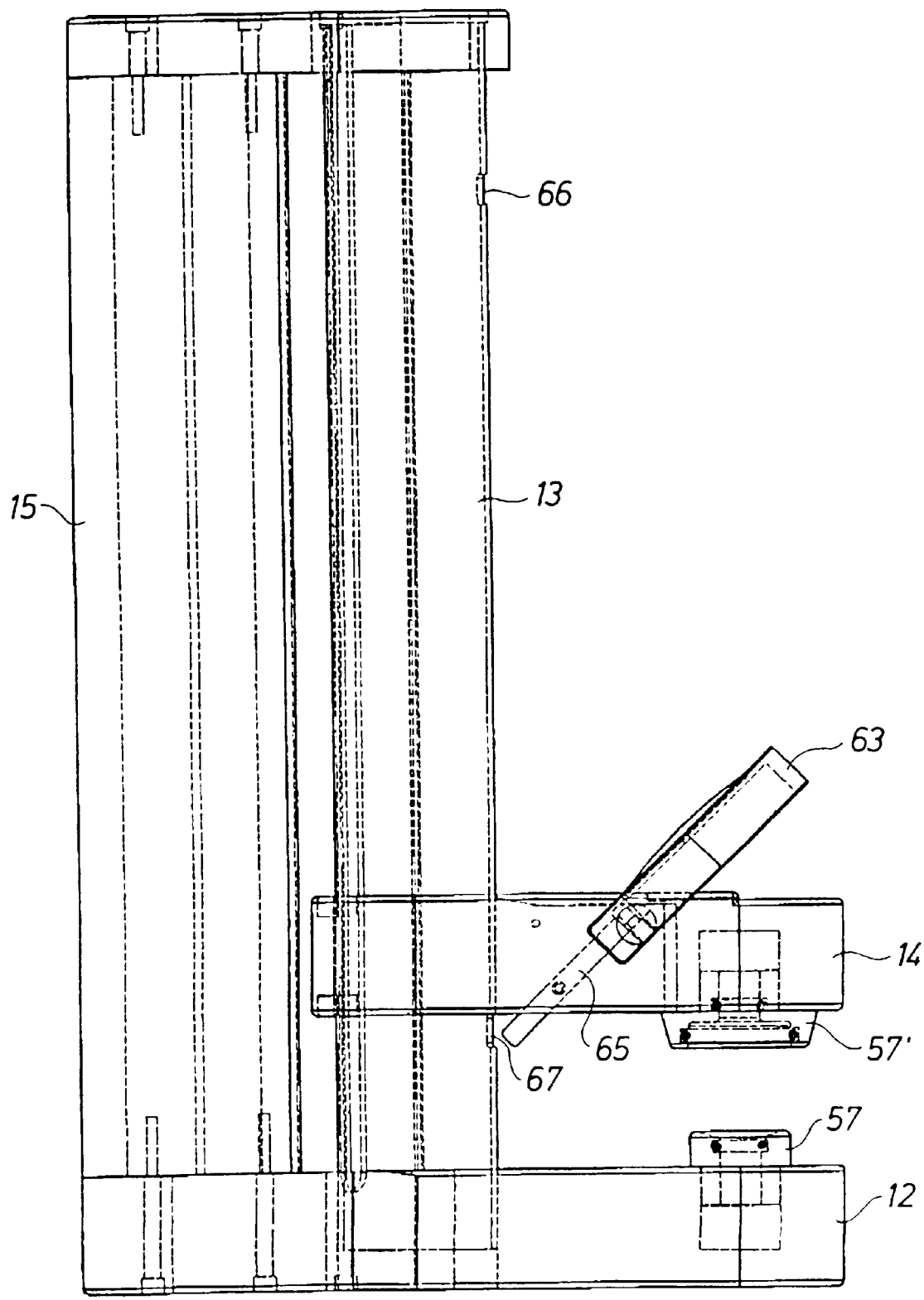
Figure 16:
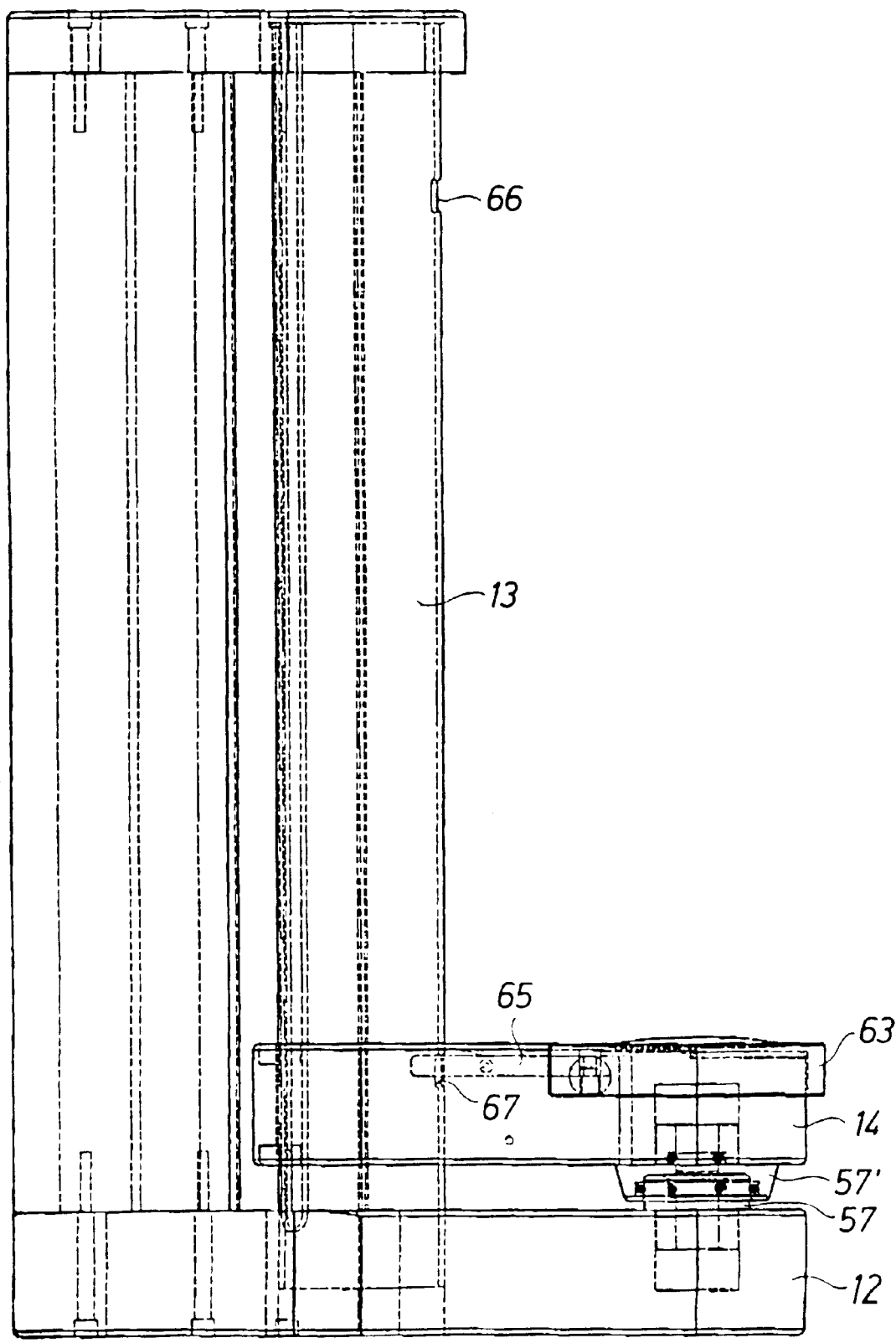
Figure 17:
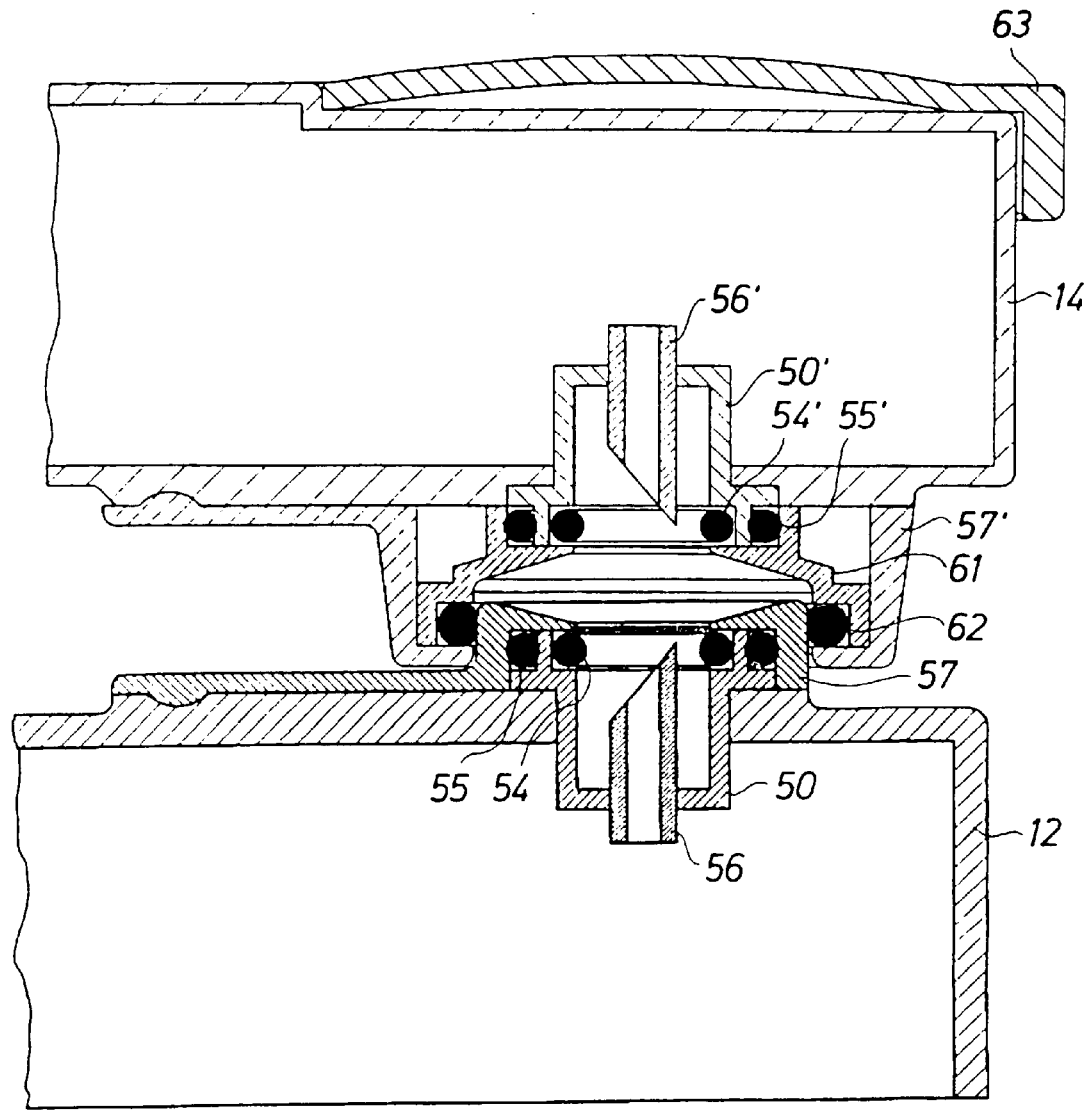
Figure 18:
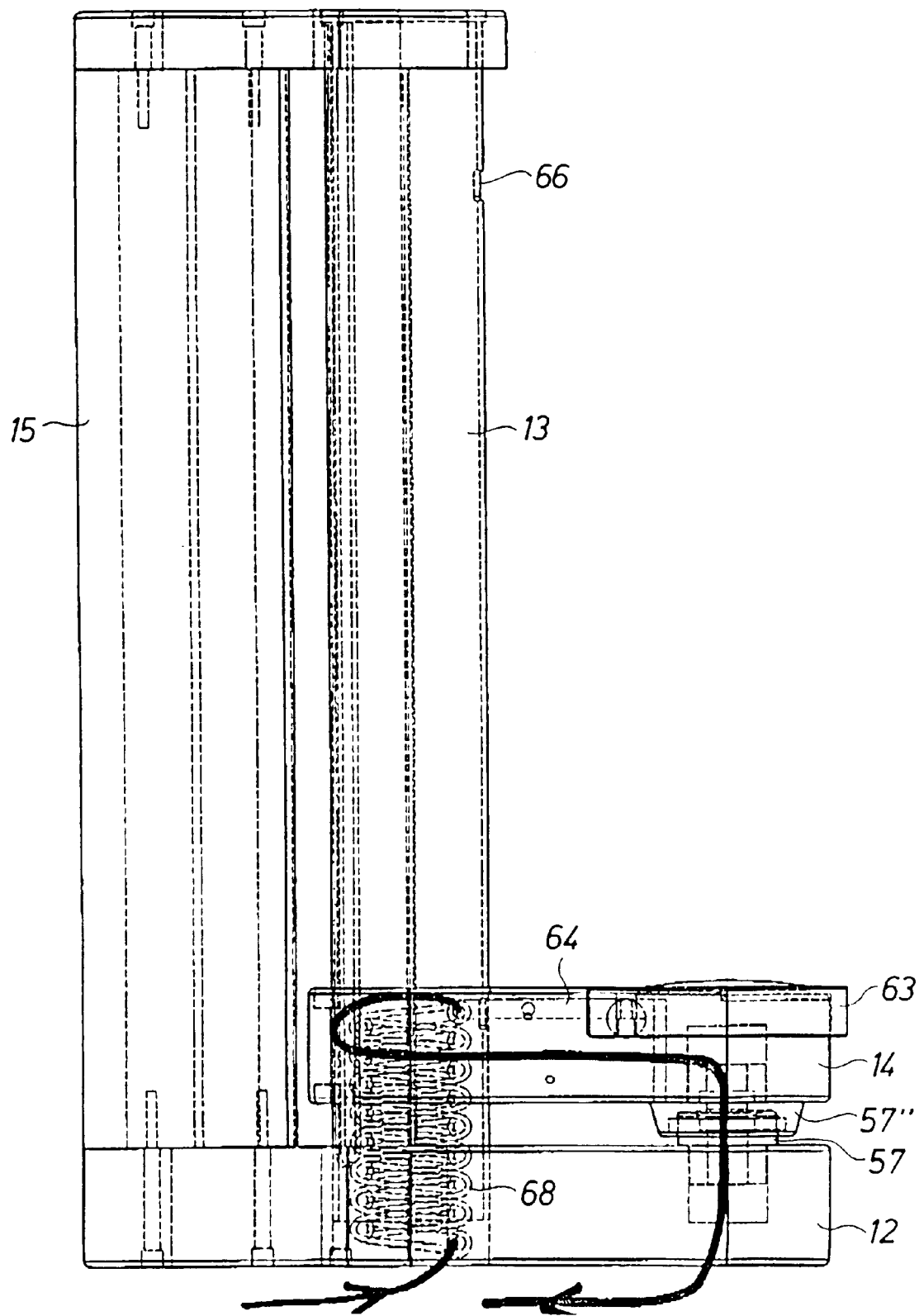

In order to explain the invention in more detail an illustrative embodiment will be described with reference to the accompanying drawings in which FIG. 1 is a perspective view of a dialysis machine with the device according to the invention, FIG. 2 is a side view of the powder cartridge mounted in the dialysis machine, FIG. 3 is an exploded perspective view of the powder cartridge, FIG. 4 is an enlarged axial cross-sectional view of the lower portion of the powder cartridge with neck and screw cap, a valve provided in the screw cap being in closed position, FIG. 5 is a perspective view of the holder for the powder cartridge, FIG. 6 is an exploded perspective view of the lower jaw of the holder, FIG. 7 is a vertical cross-sectional view of the lower jaw of the holder, FIG. 8 is an exploded perspective view of the upper jaw of the holder, FIG. 9 is a vertical cross-sectional view of the upper jaw of the holder, FIG. 10 is a side view of the holder without the powder cartridge, FIG. 11 is a side view of the holder with the powder cartridge mounted therein FIG. 12 is an axial cross-sectional view of the lower end of the powder cartridge similar to FIG. 4 but with the valve in a open position, FIG. 13 is a side view similar to FIG. 11 but without the powder cartridge, illustrating the liquid flow, FIG. 14 is a plan view of the holder and the upper jaw illustrating the water flow, FIG. 15 is a side view of the holder with the upper jaw displaced to a lower position, FIG. 16 is a side view of the holder with the jaws interengaged for performing a rinsing and disinfection cycle, FIG. 17 is an enlarged vertical cross-sectional view of the jaws in the position of FIG. 16, and FIG. 18 is a view similar to FIG. 16 disclosing the water flow during the rinsing cycle.

In FIG. 1 in the drawing there is disclosed a dialysis machine 10 which is supposed to be of the type DrakeWillock® system 1000™ and in the present case is set up to operate with preparation of dialysis liquid from a powder concentrate (sodium bicarbonate), which in an amount intended for one or more treatments is enclosed in a disposable cartridge 11. This cartridge is mounted to the machine between a stationary lower jaw 12 and a movable upper jaw 14 which can be displaced towards and away from the lower jaw on a tubular guide 13. Said guide is supported by an holder 15 which is mounted to a vertical mounting rail 16 provided externally on the machine. Means not shown in detail in FIG. 1 are provided for conducting water through the cartridge for dissolving the powder in the water as is known per se in connection with dialysis machines.

Cartridge 11, FIGS. 2 and 3, is cylindrical with semi-spherically domed end portions and is made up of two parts 11A and 11B of injection molded plastics, preferably polypropylene, which are interconnected by mirror welding at outwardly projecting circumferential flanges 17A and 17B, respectively. One part 11A, the upper part, which has a larger axial length than the other part 11B such that the joint between the parts at flanges 17A and 17B is not located midway of the cartridge forms a central circular hollow stud in the domed end, said stud comprising a portion 18 connecting to part 11A and having a larger diameter, and a portion 19 projecting therefrom and having a smaller diameter, the hollow stud thus formed communicating with the interior of the cartridge and being closed at the outer end thereof by means of a membrane 20 formed as an end wall on the stud.

The other part 11B of the cartridge forms in the domed end thereof a central circular neck 21 having an external screw thread 22. The neck joins a circular axially directed collar 23 which has internally a smooth cylindrical surface 24 and has externally a circumferential row of a saw teeth 25. A cap 26 having a grooved or knurled outside surface and internal screw threads 27 is dimensioned to be screwed onto the neck and has an end wall 28 which is connected with the rest of the cap by means of a number of shear webs 29 distributed over the circumference of the cap a small slit or cut 30 being provided between the end wall and the rest of the cap said slit or cut being bridged by the shear webs 29. The cap with end wall 28 and shear webs 29 is injection molded in one piece of plastics, preferably the same plastics as that the cartridge is made of, viz. polypropylene. End wall 28 forms a circular hollow stud 31 projecting centrally from said end wall said stud being closed in the outer end thereof by means of a membrane 32 forming an end wall of the stud.

End wall 28 has internally a circular row of saw teeth 33 which are, however, inclined in the opposite direction to teeth 25 on the neck. Moreover, end wall 28 forms an internal annular bulge 34 having an outwardly directed cylindrical surface 35. A valve element 36 is mounted on bulge 34 said valve element comprising a circular ring 37 with a cylindrical axially directed collar 38. This collar is so dimensioned that it fits on the inside thereof against surface 35, and it has on the inside an annular bead 39 which snaps into an annular groove in surface 35 when the valve element is mounted on bulge 34 in the correct position thereof. The valve element comprises also a valve member 40 which is cylindrical but at a conical portion 41 merges from a portion 42 having a larger diameter, into a portion 43 having a smaller diameter, said latter portion having an outside diameter which is smaller than the inside diameter of hollow stud 31 so that portion 43 can project into said stud, and terminates at an end wall 44 at the lower end of the valve member. At the other, upper end thereof the valve member is connected with ring 37 by means of four thin resiliently flexible arms 45 so that the valve member 40 can be moved axially in relation to the ring 37. When the valve element is mounted on bulge 34 the narrower portion 43 of valve member 40 projects into stud 31 the conical portion 41 resting under a certain pressure against the inside of end wall 28 where this joins stud 31, due to under the spring bias of arms 45 which are dimensioned to exert in this position of the valve member sufficient pressure on said member in order that the valve member will be kept in sealing engagement with end wall 28. Also valve element 36 preferably is injection molded of polypropylene.

A woven or injection molded filter net 46 also preferably of polypropylene is located in a recess in the upper surface of ring 37 and is connected to the ring by ultrasound welding.

After the cartridge thus constructed having been pressure tested for control of the tightness of the weld between flanges 17A and 17B an amount of powder (sodium bicarbonate) intended for a single dialysis treatment or several dialysis treatments is filled into the cartridge through neck 21, cap 26 then being screwed onto the neck until end wall 28 thereof engages the end surface of the neck. Then, the smooth inside surface 24 of collar 23 fits against the outside surface of collar 38 which has an annular bead 47 for sealing between collar 38 of the valve element and collar 23 of the neck. Collar 38 is clamped between surfaces 24 and 35 on collar 23 and bulge 34, respectively, securing necessary sealing between valve element 36 and neck 21 and between valve element 36 and bulge 34, respectively. Neck 21 has a radial flange 48 which at a flared edge portion 49 sealingly engages the upper surface of filter net 46 in the peripheral region thereof and also serves to locate valve element 36 in the cap when it is screwed on. Just before the cap is completely screwed on teeth 25 and 33 will interengage but these teeth shall be so orientated that they allow the cap to be screwed on, the teeth 33 of the cap rasping over teeth 25 on the neck without engaging therewith. The cartridge is then completely closed for storage and transport until it is connected to the dialysis machine. All parts of the cartridge including the net, valve element and cap, should be made of one and the same plastics and as mentioned above a suitable material is polypropylene.

The holder comprising jaws 12 and 14 in FIG. 1 in which the cartridge described shall be mounted will now be described with reference to FIGS. 5 to 11 and 13 to 18. The stationary jaw 12 is provided with a bushing 50 which is inserted into an aperture 51 in the jaw and at a shoulder formed by an outside flange 52 on the bushing rests on the upper surface of the jaw. In an enlarged portion 53 a gasket in the shape of an O-ring 54 is located, and on flange 52 a further gasket in the shape of an O-ring 55 is located. Inside bushing 50 there is provided a tube 56 which can be attached to the bushing or be integral therewith. The upper end of the tube is made tapering by being obliquely cut off similar to a cannula while the lower end of the tube is adapted to be connected to a hose. A lid 57 having a central opening 58 is provided over bushing 50 and is mounted to jaw 12 by means of bayonet coupling means 59 for engagement into matching slots 59A in the jaw. An arm 57A with a projection 57B on the lower side thereof is provided on lid 57, and when the lid has been located and the bayonet coupling has been engaged by turning the lid projection 57B is received in a depression 60 in the jaw. Arm 57A is sufficiently resilient so that projection 57B when the lid is being rotated in order to disengage the bayonet coupling can slide on the upper surface of the jaw and then snap into the depression 60 when the lid is locked in position. Lid 57 maintains O-rings 54 and 55 in position in the jaw.

The upper jaw has a similar arrangement; earlier described elements have been given corresponding reference numbers with the addition of a prime sign. In this case there is, however, also provided a ring 61 and a seal in the shape of an O-ring 62. Lid 57' which in this case has a larger diameter than lid 57 on the lower jaw keeps ring 61 pressed against the jaw while the ring in turn maintains bushing 50' in opening 51' and also maintains O-rings 54' and 55' in position. O-ring 62 located between ring 61 and lid 57' is received by ring 61 and is maintained in position by this ring and the lid.

On the upper jaw 14 an operating member 63 is provided which can be swung upwards from the position shown in FIGS. 5 to 8 about an horizontal shaft 64 to the position shown in FIG. 10. The operating member is rigidly connected with a lever 65 inside jaw 14. When the operating member 63 is in the position shown in FIGS. 5 and 8 the free end of lever 65 engages a notch 66 in guide 13; see FIG. 11. Then, jaw 14 is kept in the position shown in FIG. 11. The operating member is arrested in this position by means of a protrusion 65A on the jaw, which engages a depression 65B on arm 65. When the operating member 63 is swung upwards jaw 14 will initially be moved two cm or so upwards along guide 13 by means of lever 65 engaging notch 66 said notch 66 in guide 13 forming an abutment for the jaw to be raised. If the operating member 63 is swung further upwards to the position according to FIG. 10 wherein the operating member is arrested by another protrusion 65C on jaw 14 engaging depression 65B, lever 65 will be disengaged from notch 66 and jaw 14 can now be displaced freely downwards along guide 13. When jaw 14 has been displaced downwards towards the stationary jaw 12, FIG. 15, it will be in a lower position, FIG. 16, when the operating member 63 is folded down with lever 65 engaging a notch 67 in guide 13.

An helical hose 68, FIGS. 13 and 14, which is located in the tubular guide 13 is, at the ends thereof, anchored to the lower and the upper jaw 12 and 14, respectively, and communicates below with a water conduit (not shown) in the dialysis machine 10 and at the top with tube 56' in the upper jaw 14 for supply of water to said tube 46' while another hose (not shown) is connected to tube 56 in the lower jaw 12 to be connected to the dialysis machine at a position where concentrated sodium bicarbonate solution shall be supplied for use in the dialysis machine.

The cartridge 11 described filled with powder and closed by means of capsule 26 is mounted between jaws 12 and 14 as shown in FIG. 11 and indicated by dot-and-dash lines in FIG. 13 in the following manner.

The upper jaw 14 is displaced upwards two cm or so by the operating member 63 being swung upwards, FIG. 10, and with the upper jaw in this position cartridge 11 at stud 31 on screw cap 26 is passed through the central opening in lid 57 on the lower jaw 12 and into socket 50. O-ring 54 will seal around stud 31. The pointed end of tube 56 is moved against end wall 32 and sufficient pressure is exerted on the cartridge in order that this end wall will be penetrated and will yield. The end wall has a circular shear line in order to be folded upwards as a pivoted lid when tube 56 is pressed against the end wall as is indicated in FIG. 4 by dot-and-dash lines. Tube 56 has such length that when screw cap 26 engages lid 57 on the lower jaw 12 the tube engages valve member 40 and has lifted said member from the seat thereof on end wall 28 against the spring bias of arms 45. After this application of the lower end of the cartridge on the lower jaw 12 operating member 63 is pressed down towards the position disclosed in FIG. 11 the movable upper jaw 14 being moved downwards receiving portion 19 having the smaller diameter of the hollow stud in the upper end of cartridge 11, in bushing 50' in the upper jaw 14 O-ring 54' sealing around the stud. At the insertion the pointed end of the cannula-like tube 56' will penetrate end wall 20 of the hollow stud. Sealing ring 62 is not effective in this position because portion 18 having the larger diameter of the hollow stud in the upper end of the cartridge has a considerably smaller diameter than the central opening in lid 57, on the upper jaw 14. Now, the cartridge is mounted between tube 56' on the upper jaw 14 and tube 56 on the lower jaw 12 to conduct water through the cartridge for dissolving the powder enclosed therein into the water for the performance a dialysis treatment. The solution discharged from the cartridge is a concentrate which will be diluted with water in the machine to the concentration required for the treatment. The liquid flow is disclosed in FIG. 13 where cartridge 11 is indicated with dot-and-dash lines only. However, the arrows in FIG. 12 will show that the liquid from the cartridge flows through neck 21, further through filter net 46 to and through the passage defined by means of collars 23 and 38 the liquid passing between arms 45 then to pass between the raised valve member 40 and the valve seat formed by end wall 28 to the hollow stud 31 and from there into tube 56. Slit or cut 30 is located outside the liquid passage.

When the treatment (or treatments) have been completed the "used" cartridge shall be removed which is effected by displacement of the upper jaw 14 upwards two cm or so by the operating member 63 being swung upwards (FIG. 10). Tube 56' on the upper jaw then will be drawn out of the hollow stud 19 at the upper end of the cartridge which then can be lifted from the lower jaw 12 the screw cap 26 being withdrawn from tube 56 and valve member 40 being again pressed against the seat thereof on end wall 28 by arms 45. This is an important function of the cartridge described because remaining liquid in the cartridge cannot flow out from the lower end of the cartridge when the cartridge is removed from the dialysis machine as is the case with existing cartridges for use in dialysis machines. Escaping liquid would of course soil the lower jaw and parts of the dialysis machine located below said jaw, which is not very nice for the people who are handling the dialysis machine. Now, the cartridge can be taken to a sink or the like where the screw cap at the lower end of the cartridge is unscrewed for emptying the cartridge. Unscrewing which is prevented per se by the locking engagement between teeth 25 on neck 21 and teeth 33 on end wall 28 of screw cap 26 cannot take place unless the shear webs 29 between end wall 28 and the rest of the screw cap are broken with the consequence that end wall 28 with valve element 36 can fall off the rest of the cap. Only an initial turning of the cap at unscrewing is necessary in order that the end wall will come loose and a free passage thus will be opened for the liquid through the cap from the interior of the cartridge. It is thus not necessary to unscrew the cap completely. As far as end wall 28 tightly adheres to the neck due to the fact that snug fit between bulge 34 on the end wall and collar 38 on the valve unit may be necessary in order to obtain satisfactory sealing therebetween it may be necessary to pull the end wall from the neck by the fingers after the initial unscrewing of the cap. As soon as the end wall has come loose and has fallen or has been pulled off the cap cannot be used for reclosing the cartridge, and it is thus made impossible for the cartridge to be filled again with powder at the site of use with following risk of wrong dosage, filling of wrong powder, or contamination of the interior of the cartridge.

The cartridge must thus be discarded after having been used once but the material thereof just as the material of the screw cap including the end wall and the valve element can be recovered and can be collected for recovery in a particulary convenient manner if the two parts as has been mentioned for the preferred embodiment consist of one and the same material for example polypropylene.

After each dialysis treatment a rinsing and disinfection cycle is effected in the dialysis machine disinfection liquid being passed from one jaw to the other without passing through a cartridge mounted between them. In order to effect a rinsing and disinfection cycle the upper jaw 14 is moved to the lower position in which it is engaged with the lower jaw 12 in the manner described above. Operation member 63 is swung upwards, FIG. 10, so that arm 65 disengages the upper notch 66 in guide 13, the jaw is pushed downwards along the guide under compression of hose 68 to the position according to FIG. 15, and the operating member 63 is swung downwards to engage the lower notch 67 for engaging jaw 14 with jaw 12, FIGS. 16 to 18. Then, lid 57 on the lower jaw 12 is received by the central opening in lid 57' on the upper jaw 14, FIG. 17, lid 57 on the lower jaw 12 being dimensioned in such a way that the O-ring 62 on the upper jaw 14 seals against the outside of lid 57 as shown in FIG. 17. O-rings 54 and 54' have no sealing function, however, with the jaws in this position. When rinsing and disinfection liquid now is allowed to flow to the upper jaw 14 through hose 68 the flow circuit is short-circuited to the lower jaw 12 as indicated in FIG. 18. As will be seen from FIG. 17 O-rings 54 and 54' are exposed to the flowing liquid so that they will be overflown by liquid under the rinsing and disinfection cycle, which is important because these O-rings shall seal against the two end connections of the cartridge and this sealing can be jeopardized if there is precipitation or coating of bicarbonate on the O-rings. It is not necessary, however, to rinse O-ring 62 because it has no sealing function in connection with the dialysis procedure itself.

The O-rings can all easily be exhanged when necessary by lids 57 and 5', respectively, thanks to the bayonet coupling easily being removed from the associated jaw as is necessary in order to get access to the O-rings for exchange. Also bushings 50 and 50' with tube 56 and 56', respectively, for the same reason can be easily exchanged if this would be necessary due to the fact that the pointed end of the tube has become blunt after use for some time. The holder for the cartridge is thus well suited for maintenance and repair works.

The embodiment described can be modified within the scope of the claims thus, the valve in the screw cap can be constructed in another manner.

In the embodiment shown the sealing rings are kept in position by means of a lid which is removably mounted to the jaw by means of a bayonet coupling but a quick coupling of another type can be provided for mounting the lid which can also be constructed to be screwed onto a hollow stud on the jaw.

The device for locking the movable jaw in different positions on the guide can also be constructed in another manner than that shown herein. The movable jaw can be constructed to be clamped in different positions on guide 13 and it can also be displaceable by means of a screw/nut device or a rack/gear device. Both jaws can also be guided for parallel movement towards and away from each other by means of a link system.

Each protrusion 65A and 65C, respectively, can be replaced by a spring biassed ball mounted in a seat said ball being pressed back against the spring bias by arm 65 to snap into depression 65B.

O-rings are suitable sealing rings but sealing rings of another type can no doubt be used in the device described.

The device of the invention can also be used for mounting cartridges of another embodiment than that shown herein provided, however, with hollow studs for sealed connection with the jaws.

We claim:

1. Dialysis machine having an inlet and an outlet for liquid, and a device for exchangeable connection of a powder cartridge having a hollow stud at each of opposite ends thereof, between said inlet and said outlet, said device comprising:

first and second jaws, said first jaw being provided with said inlet and said second jaw being provided with said outlet, means for guiding at least one of said first and second jaws for linear displacement towards and away from the other jaw to respectfully engage said jaws with the powder cartridge and fluidly connect of the inlet and the outlet and disengage said jaws, wherein upon engagement of said jaws with said powder cartridge, each of said jaws is engaged, respectively, each to one of the hollow studs on the powder cartridge located therebetween, for conducting liquid through the cartridge, and to engage said first and second jaws with each other for direct interconnection of the inlet and the outlet, and sealing means on each jaw for sealing with the respective hollow stud on the powder cartridge.

2. Dialysis machine as in claim 1, wherein said sealing means comprises a sealing ring for sealing around said respective hollow stud.

3. Dialysis machine as in claim 2, further comprising an annular lid on each jaw detachably connected with the jaw for retaining the sealing ring on the jaw.

4. Dialysis maching as in claim 3, further comprising, for each jaw a bayonet coupling detachably connecting said lid with the jaw.

5. Dialysis machine as in claim 4, wherein the annular lid on one jaw is smaller than the annular lid on the other jaw to be encircled by the lid on said other jaw when the jaws are engaged with each other.

6. Dialysis machine as in claim 5, further comprising an annular sealing element in the larger lid on said other jaw for sealing between the lids when the jaws are engaged with each other.

7. Dialysis machine as in claim 6, further comprising a spacer ring on said other jaw, mounted on the jaw by means of the lid thereof.

8. Dialysis machine as in claim 7, wherein said annular sealing element for sealing between the jaws is located between the lid on said other jaw and said spacer ring.

9. Dialysis machine as in claim 3, wherein the annular lid on one jaw is smaller than the annular lid on the other jaw so as to enable said one jaw to be encircled by the lid on said other jaw when the jaws are engaged with each other.

10. Dialysis machine as in claim 9, further comprising an annular sealing element for the larger lid on said other jaw for sealing between the lids when the jaws are engaged with each other.

11. Dialysis machine as in claim 10, further comprising a spacer ring on said other jaw, mounted on the jaw by means of the lid thereof.

12. Dialysis machine as in claim 11, wherein said annular sealing element for sealing between the lids is located between the lid on said other jaw and said spacer ring.

13. Dialysis machine as in claim 1, further comprising an operating member on each of the at least one displaceable jaw adapted to engage with said guiding means for locking the respective jaw on the guide means in one or more positions.

14. Dialysis machine as in claim 13, wherein the operating member is pivotable between a locking position and an unlocking position and wherein said guide means forms a recess to be engaged by said operating member in the locking position thereof.

15. Dialysis machine as in claim 14, wherein the operating member is adapted to effect limited raising of the displaceable jaw on said guide means, when pivoted from the locking position to the unlocking position.

* * * * *